United States Patent
McEwen et al.

(10) Patent No.: US 10,758,247 B1
(45) Date of Patent: Sep. 1, 2020

(54) OPTICAL TOURNIQUET INTERFACE FOR SAFE PERSONALIZATION

(71) Applicant: Western Clinical Engineering Ltd., Vancouver (CA)

(72) Inventors: James Allen McEwen, Vancouver (CA); Michael Jameson, North Vancouver (CA); Tom Yu Chia Lai, Vancouver (CA); Rebecca Nicole Lim, Surrey (CA); Nicholas Alexander Prokopich, Surrey (CA)

(73) Assignee: Western Clinical Engineering Ltd., Vancouver (CA)

( * ) Notice: Subject to any disclaimer, the term of this patent is extended or adjusted under 35 U.S.C. 154(b) by 0 days.

(21) Appl. No.: 16/803,939

(22) Filed: Feb. 27, 2020

Related U.S. Application Data

(60) Provisional application No. 62/931,102, filed on Nov. 5, 2019.

(51) Int. Cl.
*A61B 17/135* (2006.01)
*A61B 17/132* (2006.01)

(52) U.S. Cl.
CPC ...... *A61B 17/1355* (2013.01); *A61B 17/1325* (2013.01)

(58) Field of Classification Search
CPC . A61B 17/1355; A61B 17/135; A61B 17/132; A61B 17/1322; A61B 17/1325; A61B 17/00; A61B 17/12; A61B 5/022; A61B 5/02233; A61B 5/6829; A61B 5/6824
See application file for complete search history.

(56) References Cited

U.S. PATENT DOCUMENTS

| | | |
|---|---|---|
| 4,469,099 A | 9/1984 | McEwen |
| 4,479,494 A | 10/1984 | McEwen |
| 5,439,477 A | 8/1995 | McEwen |
| 5,556,415 A | 9/1996 | McEwen et al. |
| 5,855,589 A | 1/1999 | McEwen et al. |
| 6,682,547 B2 | 1/2004 | McEwen et al. |
| 7,479,154 B2 | 1/2009 | McEwen et al. |
| 9,931,126 B2 | 4/2018 | McEwen et al. |

(Continued)

*Primary Examiner* — Christopher L Templeton
(74) *Attorney, Agent, or Firm* — Klarquist Sparkman, LLP

(57) ABSTRACT

A tourniquet apparatus having an optical tourniquet interface for safe personalization, a safe transfer key and a pressure controller. The optical tourniquet interface communicates with the pressure controller and is operable for contactlessly reading and authenticating a machine-readable instrument symbol associated with a tourniquet cuff if it matches stored instrument authentication data and for contactlessly reading machine-readable personalization data associated with the cuff. The optical tourniquet interface presents a personalization parameter value if the machine-readable instrument symbol has been authenticated. The safe transfer key enables the user to selectively transfer the presented value of the personalization parameter to the pressure controller only if the pressure controller is inoperable. The pressure controller is releasably connectable to the tourniquet cuff and responsive to the transferred value of the personalization parameter. The pressure controller is operable for automatically controlling a level of pressure in the tourniquet cuff during a pressure control time period.

26 Claims, 6 Drawing Sheets

(56) References Cited

U.S. PATENT DOCUMENTS

| | | | | |
|---|---|---|---|---|
| 2003/0036771 A1* | 2/2003 | McEwen | A61B 17/135 |
| | | | 606/202 |
| 2009/0118628 A1* | 5/2009 | Zhou | A61B 5/02225 |
| | | | 600/499 |
| 2013/0218033 A1* | 8/2013 | Quinn | A61B 5/022 |
| | | | 600/492 |
| 2015/0272452 A1* | 10/2015 | Mullin | A61B 5/02233 |
| | | | 600/301 |
| 2016/0008006 A1* | 1/2016 | McEwen | A61B 5/02233 |
| | | | 606/202 |
| 2016/0270795 A1* | 9/2016 | Krahwinkel | A61B 17/1355 |

* cited by examiner

OPTICAL TOURNIQUET INTERFACE FOR SAFE PERSONALIZATION

CROSS REFERENCE TO RELATED APPLICATION

This application claims the benefit of U.S. Provisional Patent Application No. 62/931,102, filed Nov. 5, 2019, which is hereby incorporated by reference.

BACKGROUND

Surgical tourniquet systems are commonly used to stop the flow of arterial blood into a portion of a patient's limb, thus creating a clear, dry surgical field that facilitates the performance of a surgical procedure and improves outcomes. A typical surgical tourniquet system of the prior art includes a tourniquet cuff for encircling a patient's limb at a desired location, a tourniquet instrument, and flexible tubing connecting the cuff to the instrument. In some surgical tourniquet systems of the prior art, the tourniquet cuff includes inflatable bladder that is connected pneumatically to a tourniquet instrument via flexible tubing attached to one or two cuff ports. The tourniquet instrument includes a pressure controller operable for automatically controlling pressure near a reference pressure in the connected inflatable bladder during a pressure control time period. Many types of such pneumatic surgical tourniquet systems have been described in the prior art, such as those described by McEwen in U.S. Pat. Nos. 4,469,099, 4,479,494, 5,439,477 and by McEwen and Jameson in U.S. Pat. Nos. 5,556,415 and 5,855,589.

Many studies published in the medical literature have shown that the safest tourniquet pressure is the lowest pressure that will stop the penetration of arterial blood past a specific cuff applied to a specific patient for the duration of that patient's surgery. Such studies have shown that higher tourniquet pressures are associated with higher risks of tourniquet-related injuries to the patient. Therefore, when a tourniquet is used in surgery, surgical staff generally try to use the lowest tourniquet pressure that in their judgment is safely possible.

It is well established in the medical literature that the optimal guideline for setting the pressure of a constant-pressure tourniquet is based on "Limb Occlusion Pressure" (LOP). LOP can be defined as the minimum pressure required, at a specific time in a specific tourniquet cuff applied to a specific patient's limb at a specific location, to stop the flow of arterial blood into the limb distal to the cuff. LOP is affected by variables including the patient's limb characteristics, characteristics of the selected tourniquet cuff, the technique of application of the cuff to the limb, physiologic characteristics of the patient including blood pressure and limb temperature, and other clinical factors (for example, the extent of any elevation of the limb during LOP measurement and the extent of any limb movement during LOP measurement).

The currently established guideline for setting tourniquet pressure based on LOP is that an additional safety margin of pressure is added to the measured LOP, in an effort to account for variations in physiologic characteristics and other changes that may be anticipated to occur normally over the duration of a surgical procedure.

LOP can be measured automatically using a distal flow sensor as described by McEwen in U.S. Pat. No. 7,479,154, or automatically using a dual-purpose cuff, as described by McEwen in U.S. Pat. No. 9,931,126.

Automatic measurement of LOP using a distal sensor, as described by McEwen in U.S. Pat. No. 7,479,154, utilizes a blood flow transducer that employs a photoplethysmographic principle to sense blood flow in the limb distal to the applied tourniquet cuff.

Automatic LOP measurement using a dual-purpose cuff has many advantages over the distal sensor method, as described in McEwen in U.S. Pat. No. 9,931,126. However, to obtain accurate and reliable LOP measurements, this method requires the use of a validated tourniquet cuff, suitable as both a sensor and an effector (dual-purpose). If a non-validated tourniquet cuff (not dual-purpose) is used, then the parameters for the LOP measurement may not be suitable, causing inaccurate LOP values that may result in bleed through or excessively high pressures applied, causing significant risk to the patient.

In addition, characteristics of the tourniquet cuff, such as cuff width and cuff length, whether the cuff is dual-port or dual-bladder, can be used to optimize the parameters for both the LOP measurement using a distal sensor or a dual-purpose cuff as described by McEwen in U.S. Pat. No. 7,479,154 and McEwen in U.S. Pat. No. 9,931,126, respectively; adjust the LOP safety margin; and change tourniquet settings, such as reducing the maximum reference pressure if the tourniquet cuff is a pediatric cuff.

Whether a cuff is a dual-purpose cuff or not, and the characteristics of a tourniquet cuff are examples of personalization parameters that are cuff-related that can be used to personalize and optimally configure the tourniquet instrument to increase patient safety. These personalization parameters may be entered manually into the instrument, which can be time consuming. Alternatively, as described in this invention, they may be read by the instrument automatically through an optical tourniquet interface.

Other personalization parameters that are not cuff-related may also be used. For instance, personalization parameters included in safety protocols can also be used to optimally configure the tourniquet instrument to increase patient safety by personalizing the tourniquet settings to the patient, the surgical procedure, or the surgeon. These personalization parameters as part of a safety protocol may include pressure and time settings, whether LOP measurement is required, LOP safety margin values, and maximum reference pressure. A user may select a safety protocol suitable for the patient, the surgical procedure, or the surgeon from a list of safety protocols to automatically configure the tourniquet settings.

In U.S. Pat. No. 9,931,126, McEwen et al. describe a surgical tourniquet system with a single channel for a single cuff. However, tourniquet systems are also commonly used with two channels for two cuffs or for a single cuff with two bladders. These multi-cuff or multi-bladder tourniquet systems are commonly used for surgeries involving intravenous regional anesthesia (IVRA) or bilateral procedures. In IVRA procedures, a dual-bladder cuff or a two-cuff system is used to retain an anesthetic agent after its introduction within a desired area. If the reference pressure levels or the inflation and deflation times of the dual-bladder cuff or a two-cuff system are not set properly, the anesthetic agent may enter the patient's circulatory system, causing serious injury or death. Tourniquet settings specifying the safe inflation and deflation times of the dual-bladder cuff or a two-cuff system can be specified in safety protocols.

In some surgical procedures, it is desirable to follow specific deflation sequences personalized to the patient, the surgical procedure or the surgeon. When a tourniquet cuff has been applied on a limb for a long duration, perioperative staff may deflate the tourniquet cuff for a short time period then re-inflate to allow limb reperfusion. A surgeon may desire a gradual stepped decrease in cuff pressure to control the release of toxins and metabolites. A procedure may also require the temporary reduction of pressure to check for bleeding at the surgical site. These deflation sequences can also be specified in safety protocols as another personalization parameter.

Safety protocols may be entered manually into the instrument, which can be time consuming. Alternatively, as described by this invention, safety protocol may be created through a remote device such as through an app on a mobile device then read by the instrument automatically through an optical tourniquet interface.

Since different tourniquet instruments may use different methods of determining LOP, and regulate pressure, due to hardware and/or software differences, personalization parameters described previously may be suitable for optimally configuring one type of tourniquet instrument but unsuitable or hazardous for another type of tourniquet instrument. For an example, personalization parameters intended for a single-port tourniquet instrument would not be suitable for a dual-port tourniquet instrument. Furthermore, configuring a tourniquet instrument by reading personalization parameters, such as those contained in a safety protocol, may be hazardous in certain situations, such as when the cuff is pressurized during a surgical procedure.

Therefore, there is a need for an apparatus and method to acquire personalization parameters to optimally configure a tourniquet instrument to increase patient safety by personalizing the tourniquet settings to the patient, the surgical procedure, or the surgeon, only if the personalization parameters are intended for the tourniquet instrument.

Some surgical tourniquet systems of the prior art include means for configuring the tourniquet instrument through cuff identification. McEwen in U.S. Pat. No. 6,682,547 describes a cuff identification method in which the tourniquet instrument detects cuff connectors having different colors that are indicative of the physical characteristics of the cuff, after the cuff and the instrument establishes pneumatic connection. This method has several limitations: (1) the color detection is performed at the cuff connector which is away from the instrument. Thus, the hardware used for detection is carried on the pneumatic tubing connected to the instrument and is more susceptible to damage as the pneumatic tubing may be dropped onto the floor, stepped on, or come in contact with liquids such as blood and cleaning solutions; (2) the number of detectable colored connectors are limited by their distances from each other in color space. The greater the number of different colored connectors there are, the closer they are to each other in color space, and the more likely it would be for false positives under different lighting conditions, or as the color degrades over time or due to cleaning chemicals. Therefore, the number of different cuffs that can be identified and the amount of data that can be contained in the colored connectors are limited; and (3) cuff detection requires physical contact between the cuff and the instrument through the connectors which may be hazardous if the cuff is sterile and must remain sterile.

Contactless cuff identification through RFID is described by McEwen in U.S. Pat. No. 9,931,126. However, RFID cuff identification has limitations: (1) RFID tags are susceptible to malfunction upon irradiation commonly used to sterilize tourniquet cuff assemblies; (2) misidentification may occur when more than one cuff with a different RFID tag is in close proximity to the RFID reader; and (3) RFID reader and RFID tags may incur a substantial increase in the cost of the instrument and/or the tourniquet cuff.

Other cuff identification apparatus and methods described or suggested in the prior art may have high risk of malfunction, be unreliable, add substantial cost, have limited number of cuffs that can be identified, and/or create legacy issues.

SUMMARY

Described below are implementations of an optical tourniquet interface for safe personalization that address shortcomings of conventional approaches.

According to a first implementation, a tourniquet system having an optical tourniquet interface for safe personalization comprises a tourniquet cuff assembly including a tourniquet cuff having an inflatable bladder adapted for connection to a tourniquet instrument, a machine-readable instrument symbol identifying one type of tourniquet instrument from a plurality of types of tourniquet instruments, and machine-readable personalization data representing a value of a personalization parameter for safe operation of the tourniquet cuff when connected to the identified type of tourniquet instrument; and a tourniquet instrument including an optical tourniquet interface communicating with a pressure controller and operable for contactlessly reading and authenticating the machine-readable instrument symbol if it matches stored authentication data, and further operable for contactlessly reading and selectively transferring the machine-readable personalization data to the pressure controller, wherein the optical tourniquet interface is adapted to present in a form perceptible to a user the value of the personalization parameter if the machine-readable instrument symbol has been authenticated; a safe transfer key for enabling the user to selectively transfer the presented value of the personalization parameter to the pressure controller only if the pressure controller is inoperable; and a pressure controller releasably connectable to the inflatable bladder of the tourniquet cuff and operable for automatically controlling pressure in the connected inflatable bladder during a pressure control time period.

According to a another implementation, a tourniquet apparatus having an optical tourniquet interface for safe personalization comprises an optical tourniquet interface communicating with a pressure controller and operable for contactlessly reading and authenticating a machine-readable instrument symbol associated with a tourniquet cuff if it matches stored instrument authentication data, and further operable for contactlessly reading machine-readable personalization data associated with the cuff, wherein the optical tourniquet interface is adapted to present in a form perceptible to a user the value of the personalization parameter if the machine-readable instrument symbol has been authenticated; a safe transfer key adapted for enabling the user to selectively transfer the presented value of the personalization parameter to the pressure controller only if the pressure controller is inoperable; and a pressure controller releasably connectable to the tourniquet cuff and responsive to the transferred value of the personalization parameter, wherein the pressure controller is operable for automatically controlling a level of pressure in the connected tourniquet cuff during a pressure control time period.

According to another implementation, a tourniquet apparatus having an optical tourniquet interface for safe personalization comprises an optical tourniquet interface communicating with a pressure controller and operable for contactlessly reading and authenticating a machine-readable device symbol associated with a remote personalization device if it matches stored authentication data, and further operable for contactlessly reading a machine-readable value of a personalization parameter associated with the remote personalization device, wherein the optical tourniquet interface includes a display and is adapted to present in a form perceptible to a user the value of the personalization parameter if the machine-readable device symbol has been authenticated; a safe transfer key adapted for enabling the user to safely transfer the value of the personalization parameter presented by the display to the pressure controller only if the pressure controller is inoperable; a reject key adapted for enabling the user to selectively reject the value of the personalization parameter presented by the display, thereby preventing transfer of the value to the pressure controller; and a pressure controller releasably connectable to a tourniquet cuff and responsive to the transferred value of the personalization parameter, wherein the pressure controller is operable for automatically controlling pressure in the connected tourniquet cuff during a pressure control time period.

DETAILED DESCRIPTION

Figure 1:
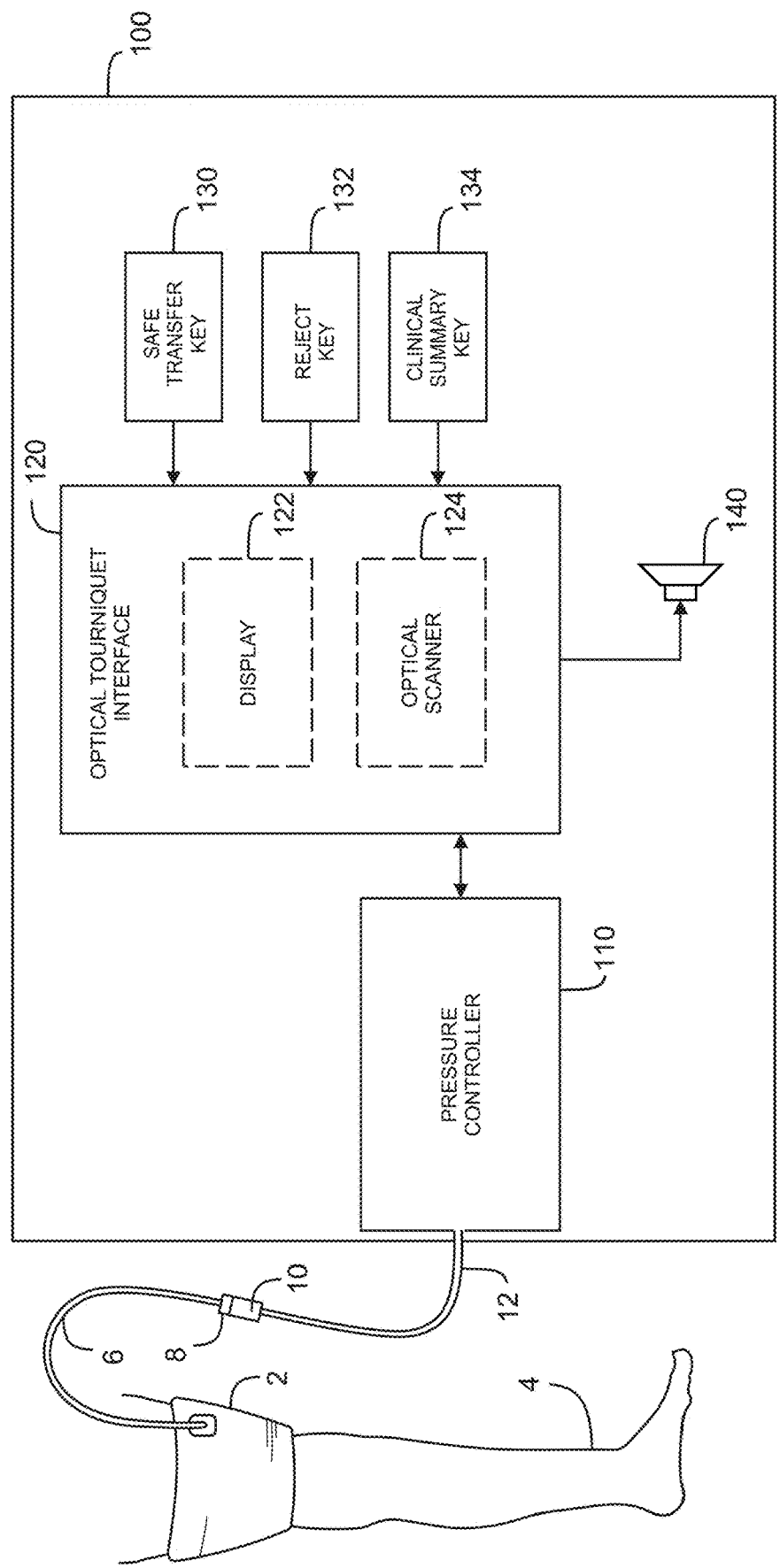
FIG. 1 is a block diagram of one implementation of a tourniquet system having an optical interface for safe personalization.

Described below are implementations of a tourniquet system that can acquire personalization parameters for safe tourniquet personalization, such as only if the personalization parameters are intended for the tourniquet instrument. Such a system can include an optical tourniquet interface that can contactlessly read a machine-readable instrument symbol that identifies one type of tourniquet instrument from a plurality of types of tourniquet instruments, and a machine-readable personalization data representing one or more values of personalization parameters on a tourniquet cuff package or a remote device. Such a system may present in a form perceptible to a user the value(s) of the personalization parameter(s) if the machine-readable instrument symbol matches stored authentication data. Such a system may include a safe transfer key or other control element, operable by the user to manually accept and transfer the value(s) of the personalization parameter(s) to the pressure controller. Such a system may also include a reject key or other control element, operable by the user to reject and prevent the transfer of the value of the personalization parameter(s) to a pressure controller. Such a system may automatically initiate actions, such as inflation or deflation, immediately or shortly after the manual or automatic transfer of the value(s) of the personalization parameter(s) to the pressure controller FIG. 1 depicts a block diagram of the tourniquet system of one representative implementation. Cuff 2 having inflatable bladder is shown encircling a limb 4 of patient. Cuff 2 may be supplied to a user as a single-use sterile cuff, packaged in a sterile tourniquet cuff assembly (see FIG. 2A), or it may be a reusable cuff. A pneumatic passageway between instrument 100 and cuff 2 is provided by cuff port 6, male locking connector 8, female locking connector 10 and flexible tubing 12. Cuff port 6 is fitted with a male locking connector 8 that mates to form a releasable pneumatic connection with female locking connector 10. Instrument 100 comprises of pressure controller 110, optical tourniquet interface 120, safe transfer key 130, reject key 132, clinical summary key 134, and speaker 140.

Pressure controller 110 includes a pneumatic pump and valve assembly and is operable for automatically controlling pressure in the connected inflatable bladder of cuff 2 near a reference pressure during a pressure control time period suitably long for a surgical procedure. Pressure controller 110 is adapted to automatically measure Limb Occlusion Pressure (LOP) of limb 4 with cuff 2.

Pressure controller 110 is also adapted to respond to values of personalization parameters transferred from optical tourniquet interface 120 to improve the safety and effectiveness of the pressure regulation, automatic LOP measurement, and other tourniquet settings. Personalization parameters include: whether cuff 2 is a dual-purpose cuff suitable for automatic LOP measurement or not; whether cuff 2 is adapted for use in a surgical procedure involving intravenous regional anesthesia or not; whether cuff 2 is single-use or reusable; the size and shape of the limb for which cuff 2 is intended to be applied to; pressure and time settings; whether LOP measurement is required; LOP safety margin values; maximum reference pressure; and other.

Pressure controller 110 records cuff 2's pressure, time, and alarm history during a surgical procedure as a plurality of pressures and alarm events of cuff 2 for a plurality of times during the pressure control time period. Upon completion of the surgical procedure, i.e., at the end of the pressure control time period, and upon activation of clinical summary key 134, optical tourniquet interface 120 communicates with pressure controller 110 to display the pressure, time, and alarm history of cuff 2 on display 122. To enable a user to capture this information remotely for later analysis, optical tourniquet interface 120 may also encode and display the information in a machine-readable form that can be optically read by a remote device, as described below. Optical tourniquet interface 120 may also encode and display values of personalization parameters in a machine-readable form.

Optical tourniquet interface includes display 122, and optical scanner 124. Display 122 may include a touchscreen to allow a user to interface with optical tourniquet interface 120. Optical tourniquet interface 120 communicates with pressure controller 110 to allow a user to control the operation of instrument 100.

Display 122 displays information to the user including reference pressure, current pressure, elapsed time, and alarm messages. Optical scanner 124 is adapted to contactlessly acquire values of personalization parameters for safe personalization, only if the personalization parameters are intended for instrument 100, as described below. If the personalization parameters are not intended for instrument 100, pressure controller 110 may use a predetermined stored value of the personalization parameter. In addition, optical tourniquet interface 120 may notify to the user through display 122 and/or speaker 140.

Once values of personalization parameters are acquired, instrument 100 allows the user to activate safe transfer key 130 to selectively transfer the values of the personalization parameters to pressure controller 110. Instrument 100 further allows the user to activate reject key 132 to reject transfer of the values of personalization parameters to pressure controller 110.

Safe transfer key 130, reject key 132, and clinical summary key 134 may be mechanical buttons on instrument 100 or they may be incorporated as touchable keys on a touchscreen of display 122.

Figure 2A:
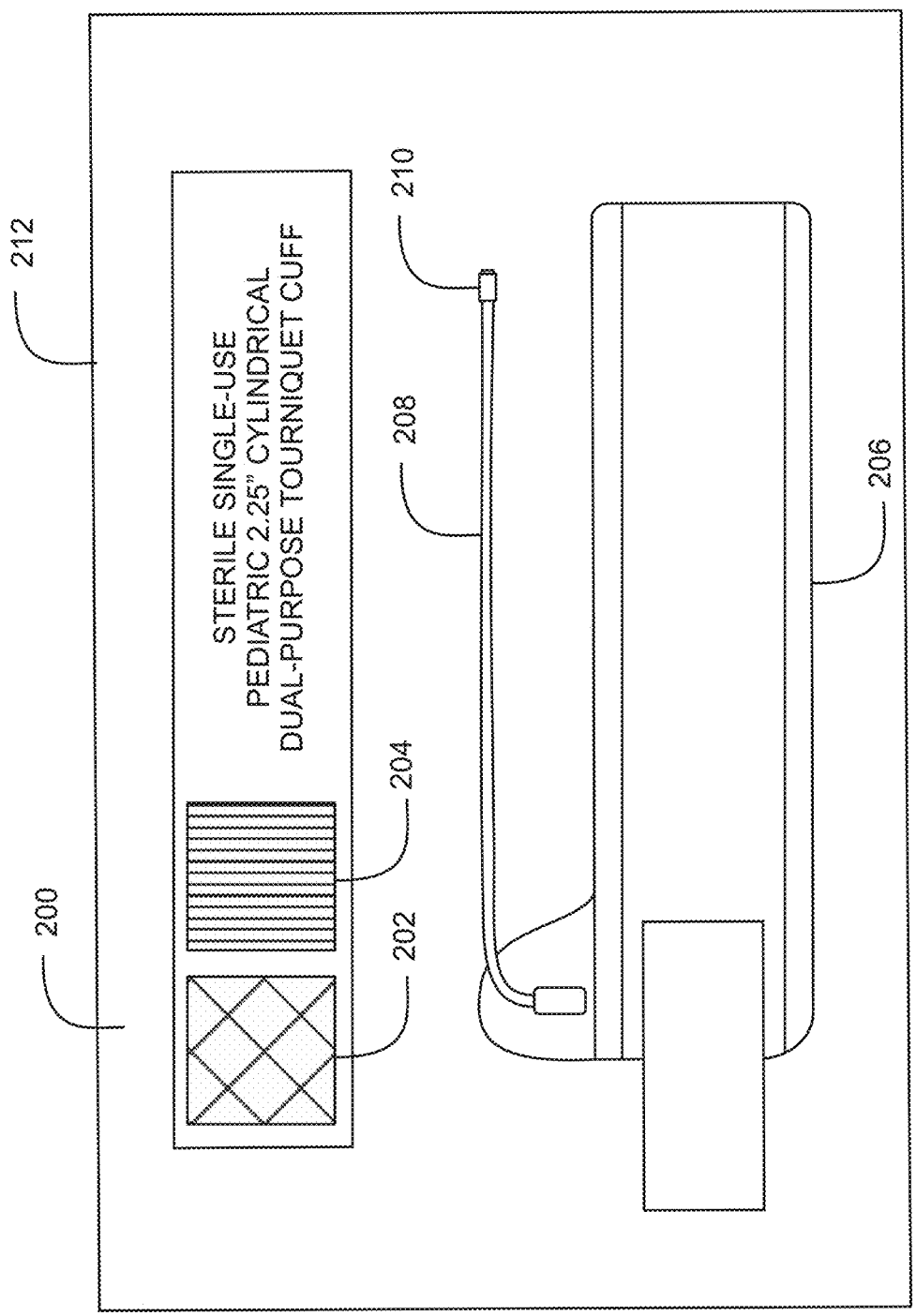
FIG. 2A is a schematic plan view showing a sterile tourniquet cuff assembly having a machine-readable instrument symbol, machine-readable personalization data and a sterile pediatric cuff.
Figure 2B:
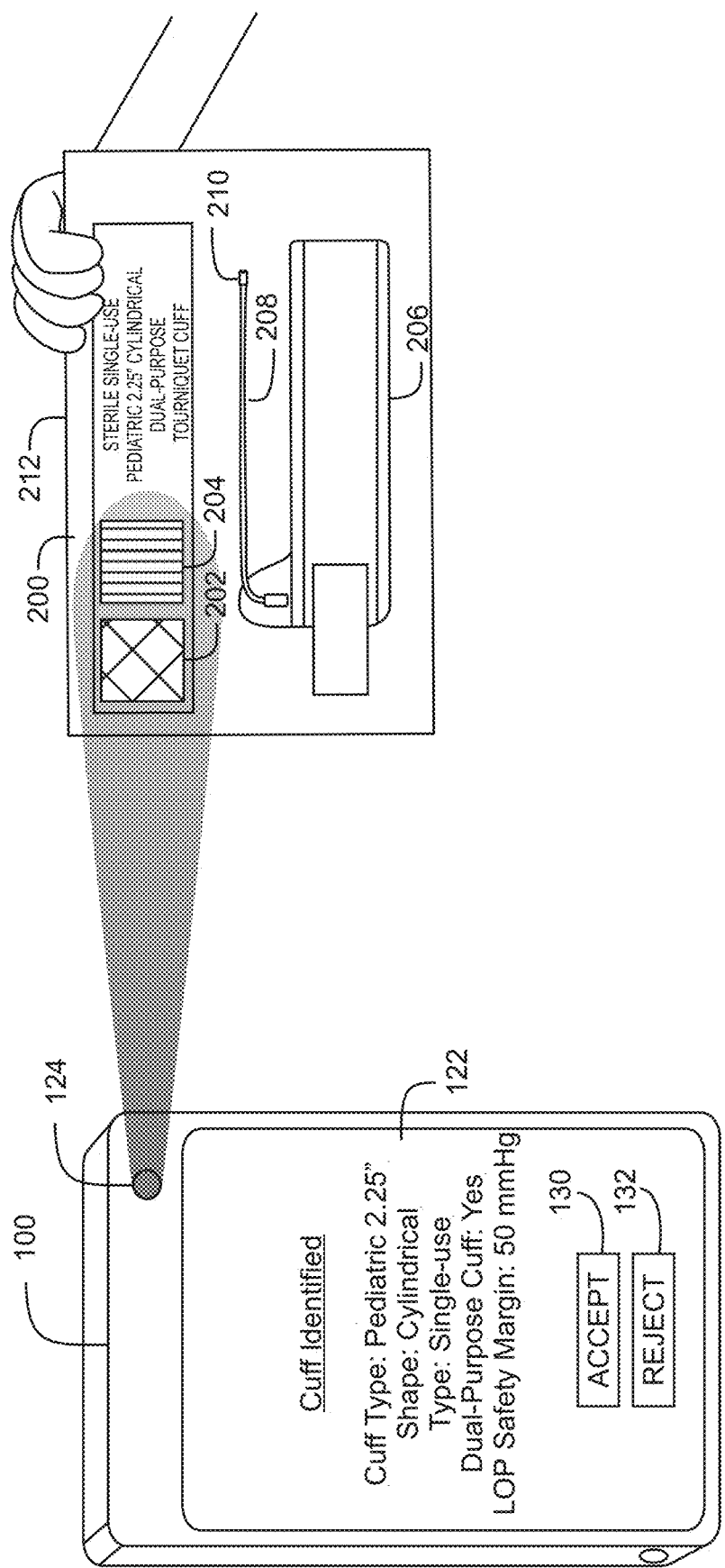
FIG. 2B is a pictorial representation of the sterile tourniquet cuff assembly from FIG. 2A being used with an instrument.

FIGS. 2A and 2B depict an example of the preferred embodiment in use.

FIG. 2A shows a sterile tourniquet cuff assembly 200 having machine-readable instrument symbol 202, machine-readable personalization data 204, and sterile single-use pediatric cuff 206 having an inflatable bladder adapted for connection to instrument 100. Cuff 206 includes sterile cuff port 208 and sterile male locking connector 210. Sterile male locking connector 210 is adapted for releasably connecting cuff 206 to instrument 100. Sterile tourniquet cuff assembly 200 includes a sterile barrier 212 to ensure the sterility of cuff 206 before use.

Machine-readable instrument symbol 202 and machine-readable personalization data 204 may be texts, images, barcodes or other marks identifiable and readable by optical scanner 124. Machine-readable instrument symbol 202 and machine-readable personalization data 204 may be encoded together in a single marking instead of two separate markings. Different techniques of encoding will be apparent to those skilled in the art. Machine-readable instrument symbol 202 and machine-readable personalization data 204 may be located on a tourniquet cuff assembly, as shown in FIG. 2A, and/or on a cuff itself, for instance, as part of a label on a reusable cuff.

Machine-readable personalization data 204 represents at least one value of a personalization parameter that is used to optimally configure instrument 100 to increase patient safety by personalizing the tourniquet settings for an individual patient, surgical procedure, or surgeon. In this example, personalization parameters include information indicating cuff 206 is a single-use, cylindrical pediatric cuff with a cuff width of 2.25". Furthermore, cuff 206 is a dual-purpose cuff and thus automatic LOP measurement using a dual-purpose cuff is enabled. Since the detected cuff is a pediatric cuff, the LOP safety margin is 50 mmHg.

Since different tourniquet instruments may use different methods of determining LOP, and regulate pressure, due to hardware and/or software differences, personalization parameters may be suitable for optimally configuring one type of tourniquet instrument but unsuitable or hazardous for another type of tourniquet instrument. For an example, personalization parameters intended for a single-port tourniquet instrument would not be suitable for a dual-port tourniquet instrument. Machine-readable instrument symbol 202 identifies the type of tourniquet instrument that is suitable for using the values of personalization parameters represented by machine-readable personalization data 204 from a plurality of tourniquet instruments.

FIG. 2B shows instrument 100 with display 122 and optical scanner 124. When a user positions sterile tourniquet cuff assembly 200 within the field of view of optical scanner 124, optical scanner contactlessly reads machine-readable instrument symbol 202 and machine-readable personalization data 204. The field of view of optical scanner 124 is optimized to encompass a predetermined range of distances and a predetermined range of orientations relative to optical scanner 124 to prevent inadvertent hazardous reading of a second tourniquet cuff assembly outside the predetermined ranges.

Optical tourniquet interface 120 authenticates machine-readable instrument symbol 202 by matching it to stored authentication data. Once machine-readable instrument symbol 202 is authenticated, optical tourniquet interface 120 displays the values of the personalization parameters through display 122. The user may review the values of the personalization parameters and if they are considered safe and appropriate for the surgical procedure, the user can then selectively transfer the presented values of the personalization parameters to pressure controller 110 through safe transfer key 130. The user may also reject the transfer of the presented values of the personalization parameters to pressure controller 110 through reject key 132.

If machine-readable instrument symbol 202 does not match stored authentication data, pressure controller 110 may use predetermined stored values of personalization parameters, or prompt the user to manually enter values of personalization parameters. In addition, optical tourniquet interface 120 may indicate to the user that an unknown machine-readable instrument symbol has been read through display 122 and/or speaker 140.

To ensure tourniquet settings are not altered inadvertently in certain situations which may be hazardous, such as changing the reference pressure while cuff 206 is pressurized, safe transfer key 130 only allows the transfer of the values of the personalization parameters to pressure controller 110 when pressure controller 110 is inoperable. Optical tourniquet interface 120 may also prevent optical scanner 124 from scanning machine-readable instrument symbol 202 and machine-readable personalization data 204 when pressure controller 110 is operable.

Once the values of the personalization parameters are transferred to pressure controller 110, instrument 100 may immediately utilize the values of the personalization parameters and initiate certain actions, such as inflation or a measurement of LOP. Alternatively, instrument 100 may wait for additional user inputs before initiating new actions.

Figure 3A:
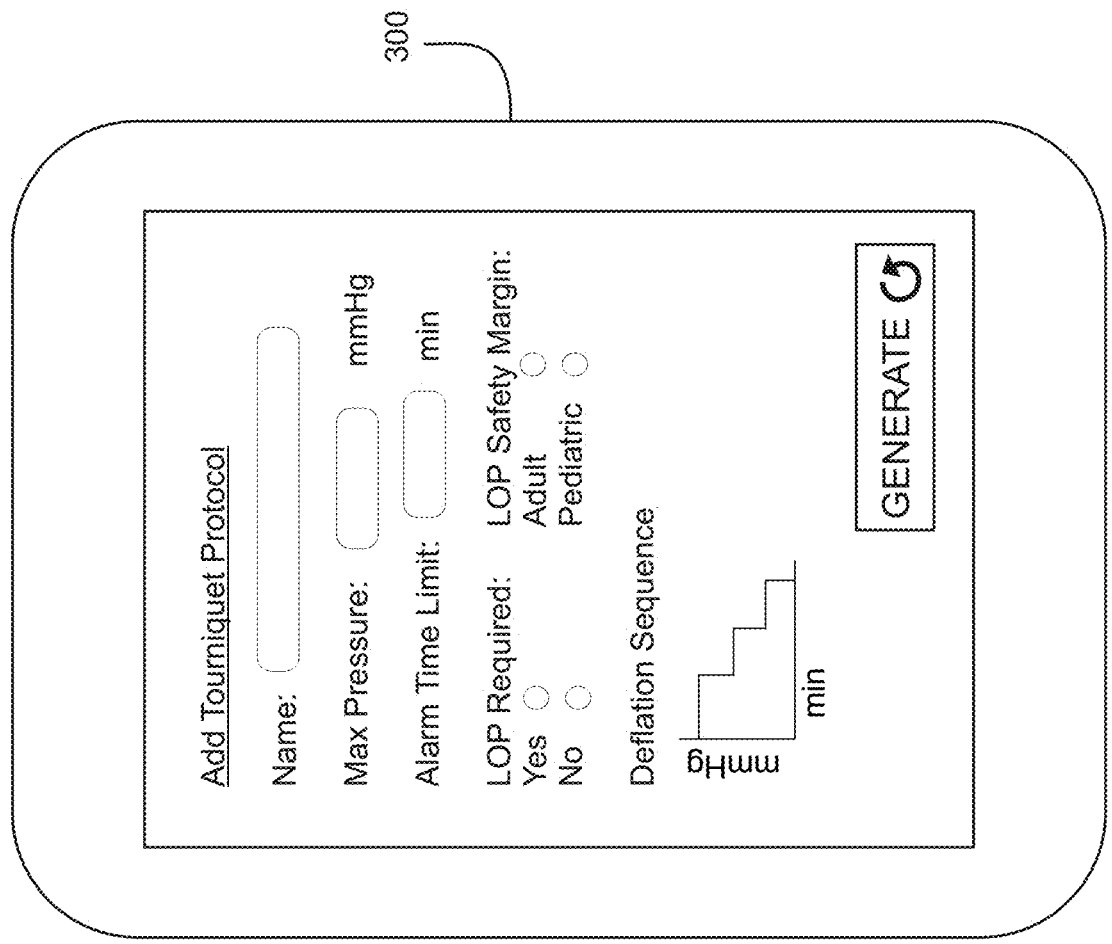
FIG. 3A is a drawing of a representative remote device having a machine-readable remote device symbol and a machine-readable data.
Figure 3B:
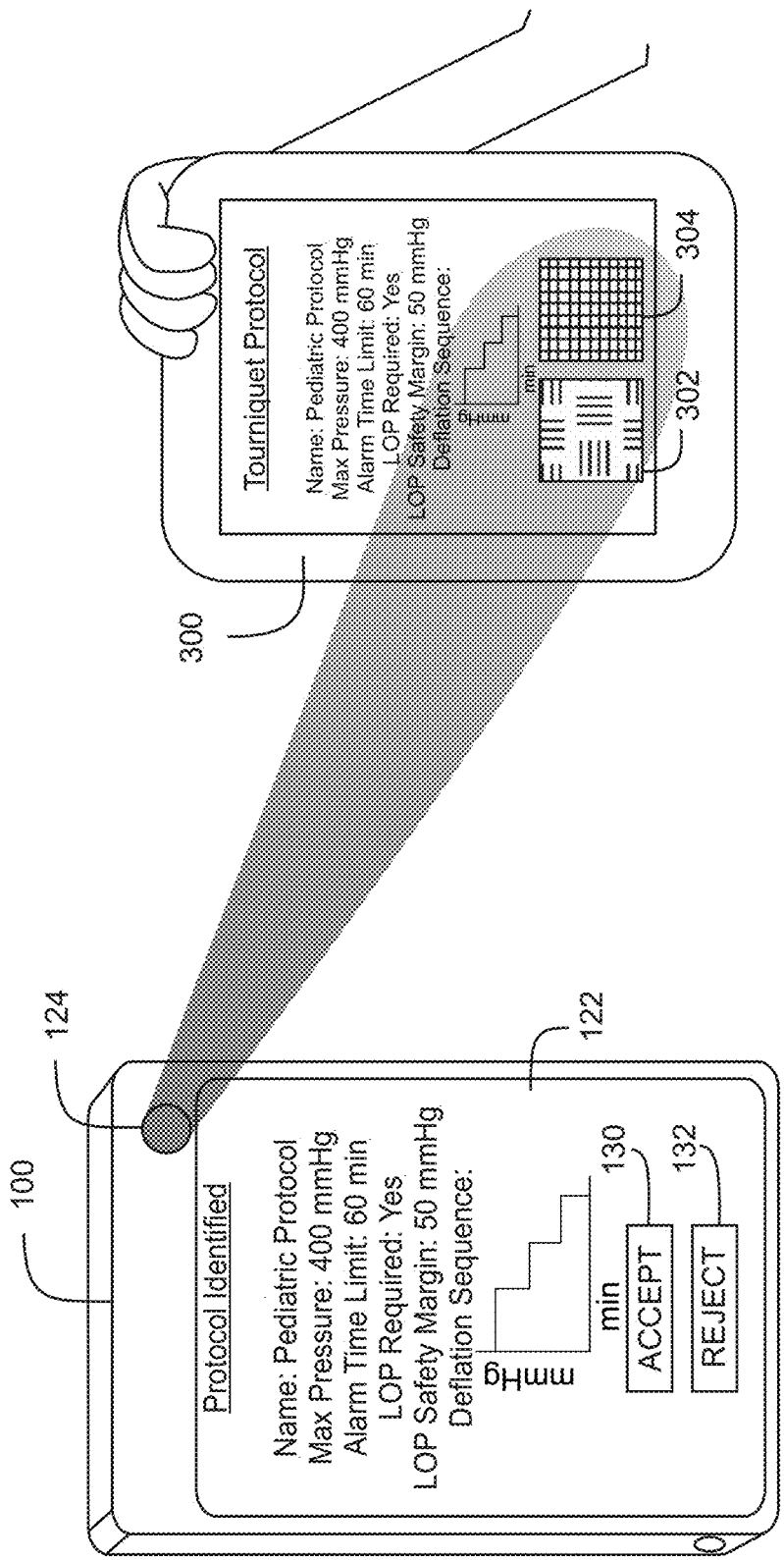
FIG. 3B is a pictorial representation of the remote device from FIG. 3A being used with the instrument.

FIGS. 3A and 3B depict another example of the preferred embodiment in use.

FIG. 3A shows remote device 300 having a touchscreen for a user to generate a safety protocol. Safety protocol includes personalization parameters that can be used to optimally configure instrument 100 to increase patient safety by personalizing the tourniquet settings to the patient, the surgical procedure, or the surgeon. FIG. 3 A shows remote device 300 allowing the user to define the following personalization parameters: the name of the protocol; the maximum reference pressure limit; the alarm time limit; whether LOP measurement is required; whether LOP safety margin is for an adult or a pediatric patient; and the deflation sequence. In the preferred embodiment, remote device 300 is a smart-phone.

FIG. 3B shows instrument 100 with display 122 and optical scanner 124. After the generation of a safety protocol from FIG. 3A, remote device 300 shows machine-readable remote device symbol 302 corresponding to remote device 300, and machine-readable data 304 associated with remote device 300 that is indicative of at least one remote value of a personalization parameter of the developed safety protocol.

When a user positions remote device 300 within the field of view of optical scanner 124, optical scanner contactlessly reads machine-readable remote device symbol 302 and machine-readable data 304. The field of view of optical scanner 124 is optimized to encompass a predetermined range of distances and a predetermined range of orientations relative to optical scanner 124 to prevent inadvertent hazardous reading of a second remote device outside the predetermined ranges.

Optical tourniquet interface 120 authenticates machine-readable remote device symbol 302 by matching it to stored authentication data. Once machine-readable remote device symbol 302 is authenticated, optical tourniquet interface 120 displays the values of the personalization parameters through display 122. The user may review the values of the personalization parameters and if they are considered safe and appropriate for the surgical procedure, the user can then selectively transfer the presented values of the personalization parameters to pressure controller 110 through safe transfer key 130. The user may also reject the transfer of the presented values of the personalization parameters to pressure controller 110 through reject key 132. In this example, personalization parameters include information associated with a safety protocol named "pediatric protocol" such as the maximum reference pressure limit (400 mmHg), alarm time limit (60 min), whether LOP is required or not (yes), to use pediatric LOP safety margin, and to use a stepped-decrease deflation sequence, which may be used to facilitate the detection and closure of bleeding vessels.

Figure 4:
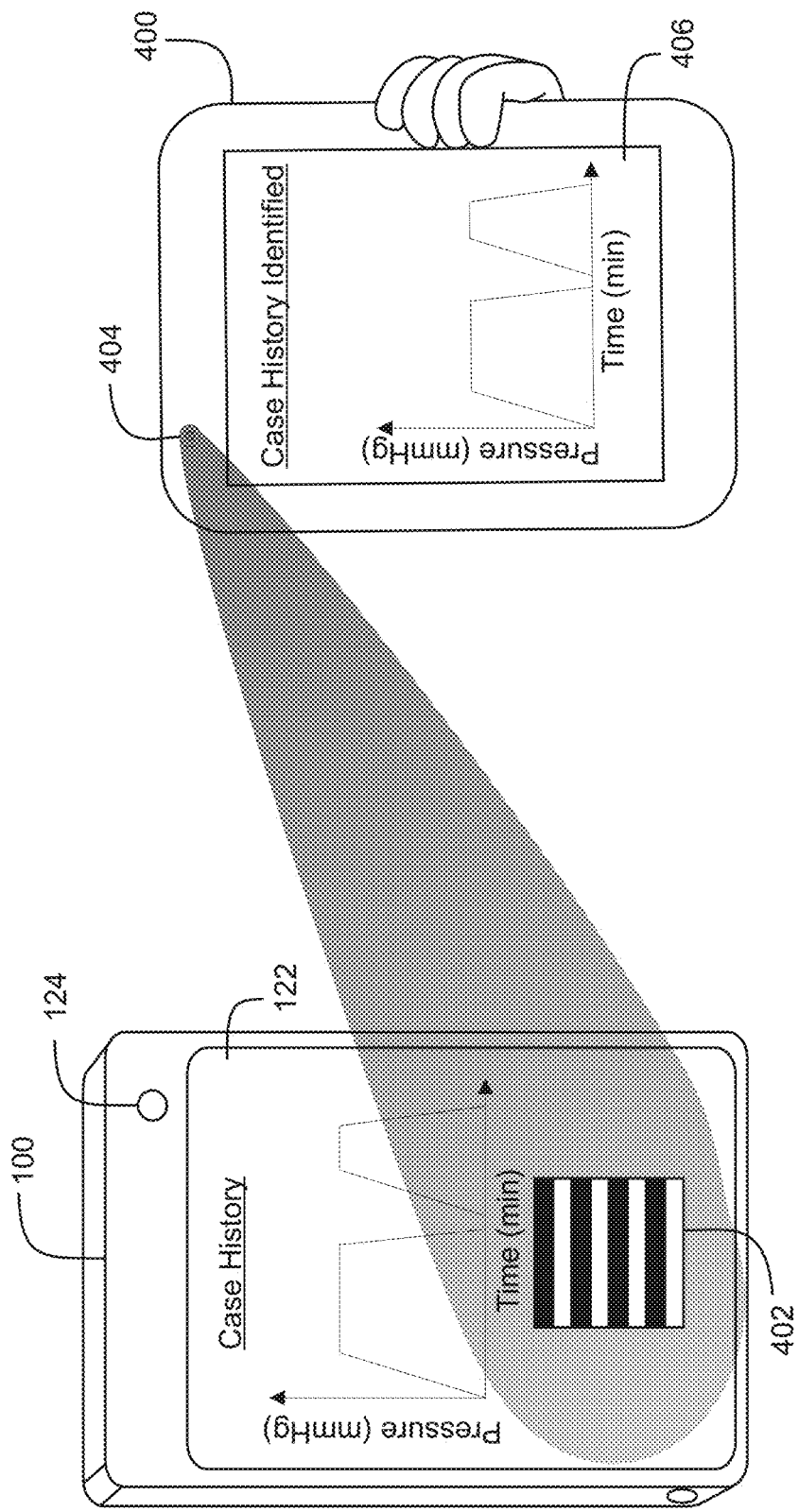
FIG. 4 is a pictorial representation of a remote device displaying a clinical summary of a surgery for future analysis as received from the instrument.

FIG. 4 depicts another example of the preferred embodiment in use.

FIG. 4 shows instrument 100 after a user activated clinical summary key 134. Clinical summary key 134 may be activated by the user after a pressure control time period, such as one suitably long for a surgical procedure. Display 122 displays a graphical representation of plurality of pressure levels and alarm events corresponding to a plurality of times during the pressure control time period. Instrument 100 also displays machine-readable clinical data 402 that is indicative of the graphical representation. Machine-readable clinical data 402 may also be indicative of previously transferred values of personalization parameters. Remote personalization device 400 is shown with remote scanner 404 capable of reading machine-readable clinical data 402, and displaying the information contained in machine-readable clinical data 402 on remote display 406. In the preferred embodiment, remote device 400 is a smart phone.

The embodiments illustrated are not intended to be exhaustive or to limit the invention to the precise form disclosed. They are chosen and described in order to explain the principles of the invention and its application and practical use, and thereby enable others skilled in the art to utilize the invention.

In view of the many possible embodiments to which the disclosed principles may be applied, it should be recognized that the illustrated embodiments are only preferred examples and should not be taken as limiting in scope. Rather, the scope of protection is defined by the following claims. We therefore claim all that comes within the scope and spirit of these claims.

We claim:

1. A tourniquet system having an optical tourniquet interface for safe personalization, comprising:
    a tourniquet cuff assembly including:
        a tourniquet cuff having an inflatable bladder adapted for connection to a tourniquet instrument,
        a machine-readable instrument symbol identifying one type of tourniquet instrument from a plurality of types of tourniquet instruments, and
        machine-readable personalization data representing a value of a personalization parameter for safe operation of the tourniquet cuff when connected to the identified type of tourniquet instrument; and
    a tourniquet instrument including:
        an optical tourniquet interface communicating with a pressure controller and operable for contactlessly reading and authenticating the machine-readable instrument symbol if it matches stored authentication data, and
            further operable for contactlessly reading and selectively transferring the machine-readable personalization data to the pressure controller
                wherein the optical tourniquet interface is adapted to present in a form perceptible to a user the value of the personalization parameter if the machine-readable instrument symbol has been authenticated;
        a safe transfer key for enabling the user to selectively transfer the presented value of the personalization parameter to the pressure controller only if the pressure controller is inoperable; and
        the pressure controller releasably connectable to the inflatable bladder of the tourniquet cuff and operable for automatically controlling pressure in the connected inflatable bladder during a pressure control time period.

2. The tourniquet system of claim 1 wherein the optical tourniquet interface includes a display and wherein the optical tourniquet interface is adapted to present the value of the personalization parameter to the user by displaying the value on the display.

3. The tourniquet system of claim 1 further including a reject key adapted for enabling the user to manually reject transfer of the value of the personalization parameter presented by a display.

4. The tourniquet system of claim 1 wherein if the machine-readable instrument symbol is not authenticated, the tourniquet instrument is configured to use a predetermined stored value for at least one personalization parameter.

5. The tourniquet system of claim 1 wherein the safe transfer key further initiates operation of the pressure controller upon the selective transfer of the presented value of the personalization parameter.

6. The tourniquet system of claim 1 wherein the machine-readable instrument symbol and the machine-readable personalization data are carried at a location on the tourniquet cuff assembly that enables contactless reading of the instrument symbol and the personalization data only if the tourniquet cuff assembly is positioned by the user within a predetermined range of distances and within a predetermined range of orientations relative to the optical tourniquet interface.

7. The tourniquet system of claim 1 wherein the value of the personalization parameter of the tourniquet cuff assembly indicates that the tourniquet cuff is adapted for automatic measurement of a Limb Occlusion Pressure of a patient by the identified tourniquet instrument.

8. The tourniquet system of claim 1 wherein the value of the personalization parameter of the tourniquet cuff assembly indicates that the tourniquet cuff is adapted for a pediatric patient.

9. The tourniquet system of claim 1 further including a remote device:
    wherein the optical tourniquet interface is further operable for contactlessly reading and authenticating a machine-readable remote device symbol associated with the remote device if it matches stored authentication data corresponding to the remote device, and wherein the optical tourniquet interface is additionally operable for contactlessly reading machine-readable data associated with the remote device that is indicative of a remote value of a personalization parameter;

wherein the safe transfer key is further adapted for enabling the user to safely transfer the remote value of the personalization parameter to the pressure controller only if the machine-readable remote device symbol has been authenticated and only when the pressure controller is inoperable; and wherein the pressure controller is further responsive to the transferred remote value for safely controlling pressure in the connected tourniquet cuff during the pressure control time period.

10. The tourniquet system of claim 1 wherein the optical tourniquet interface is further operable upon actuation of a clinical summary key by the user after the pressure control time period for generating and displaying machine-readable clinical data indicative of at least one level of pressure corresponding to a time within the pressure control time period.

11. A tourniquet apparatus having an optical tourniquet interface for safe personalization, comprising:

an optical tourniquet interface communicating with a pressure controller and operable for contactlessly reading and authenticating a machine-readable instrument symbol associated with a tourniquet cuff if it matches stored instrument authentication data, and further operable for contactlessly reading machine-readable personalization data associated with the cuff, wherein the optical tourniquet interface is adapted to present in a form perceptible to a user the value of the personalization parameter if the machine-readable instrument symbol has been authenticated;

a safe transfer key adapted for enabling the user to selectively transfer the presented value of the personalization parameter to the pressure controller only if the pressure controller is inoperable; and the pressure controller releasably connectable to the tourniquet cuff and responsive to the transferred value of the personalization parameter, wherein the pressure controller is operable for automatically controlling a level of pressure in the connected tourniquet cuff during a pressure control time period.

12. The tourniquet apparatus of claim 11 further including a sterile tourniquet cuff assembly, comprising:

a sterile tourniquet cuff;

a machine-readable instrument symbol identifying one type of tourniquet instrument from a plurality of types of tourniquet instruments and adapted for contactless reading by the optical tourniquet interface;

machine-readable personalization data representing a value of a personalization parameter for safe operation of the sterile tourniquet cuff with the identified type of tourniquet instrument and adapted for contactless reading by the optical tourniquet interface;

a sterile connector adapted for releasably connecting the sterile tourniquet cuff to the identified type of tourniquet instrument; and wherein the instrument symbol and the personalization data are carried at a location enabling contactless reading of the instrument symbol and the personalization data only if the sterile cuff assembly is positioned by the user within a predetermined range of distances and within a predetermined range of orientations relative to the optical tourniquet interface.

13. The tourniquet apparatus of claim 12 wherein the value of the personalization parameter indicates that the tourniquet cuff is adapted for automatic measurement of a Limb Occlusion Pressure of a patient by the identified tourniquet instrument.

14. The tourniquet apparatus of claim 12 wherein the value of the personalization parameter indicates that the tourniquet cuff is adapted for a pediatric patient.

15. The tourniquet apparatus of claim 12 wherein the value of the personalization parameter indicates that the tourniquet cuff is adapted for intravenous regional anesthesia of a patient's limb.

16. The tourniquet apparatus of claim 11 wherein the optical tourniquet interface includes a display and wherein the optical tourniquet interface is adapted to present the value of the personalization parameter to the user by displaying the value on the display.

17. The tourniquet apparatus of claim 11 further including a reject key adapted for enabling the user to selectively reject transfer of the presented value of the personalization parameter.

18. The tourniquet apparatus of claim 11 wherein the optical tourniquet interface is further operable upon actuation of a clinical summary key by the user after the pressure control time period for generating and displaying machine-readable clinical data indicative of at least one level of pressure corresponding to a time within the pressure control time period.

19. The tourniquet apparatus of claim 18 wherein the machine-readable clinical data is further indicative of the transferred presented value of the personalization parameter.

20. The tourniquet apparatus of claim 11 further including a remote device:

wherein the optical tourniquet interface is further operable for contactlessly reading and authenticating a machine-readable remote device symbol associated with the remote device if it matches stored authentication data corresponding to the remote device; and wherein the optical tourniquet interface is additionally operable for contactlessly reading machine-readable data associated with the remote device that is indicative of a remote value of a personalization parameter;

wherein the safe transfer key is further adapted for enabling the user to safely transfer the remote value of the personalization parameter to the pressure controller only if the machine-readable remote device symbol has been authenticated and only when the pressure controller is inoperable; and wherein the pressure controller is further responsive to the transferred remote value for safely controlling pressure in the connected tourniquet cuff during the pressure control time period.

21. A tourniquet apparatus having an optical tourniquet interface for safe personalization, comprising:

an optical tourniquet interface communicating with a pressure controller and operable for contactlessly reading and authenticating a machine-readable device symbol associated with a remote personalization device if it matches stored authentication data, and further operable for contactlessly reading a machine-readable value of a personalization parameter associated with the remote personalization device, wherein the optical tourniquet interface includes a display and is adapted to present in a form perceptible to a user the value of the personalization parameter if the machine-readable device symbol has been authenticated;

a safe transfer key adapted for enabling the user to safely transfer the value of the personalization parameter presented by the display to the pressure controller only if the pressure controller is inoperable;

a reject key adapted for enabling the user to selectively reject the value of the personalization parameter presented by the display, thereby preventing transfer of the value to the pressure controller; and the pressure controller releasably connectable to a tourniquet cuff and responsive to the transferred value of the personalization parameter, wherein the pressure controller is operable for automatically controlling pressure in the connected tourniquet cuff during a pressure control time period.

22. The tourniquet apparatus of claim 21 wherein the optical tourniquet interface is further operable upon actuation of a clinical summary key by the user after the pressure control time period for generating and displaying machine-readable clinical data indicative of at least one level of pressure corresponding to a time within the pressure control time period.

23. The tourniquet apparatus of claim 22 wherein the machine-readable clinical data is further indicative of the transferred value of the personalization parameter.

24. The tourniquet apparatus of claim 22 wherein the clinical data further includes data indicative of the duration of the pressure control time period.

25. The tourniquet apparatus of claim 21 further including the remote personalization device.

26. The tourniquet apparatus of claim 21 further comprising the tourniquet cuff connected to the pressure controller.

* * * * *